US012672769B2

(12) United States Patent     (10) Patent No.:   US 12,672,769 B2

Alatriste     (45) Date of Patent:     Jul. 7, 2026

(54) ENDOTRACHEAL INTUBATION DEVICE AND RELATED METHODS

(71) Applicant: Anthony Alatriste, Windermere, FL (US)

(72) Inventor: Anthony Alatriste, Windermere, FL (US)

( * ) Notice: Subject to any disclaimer, the term of this patent is extended or adjusted under 35 U.S.C. 154(b) by 322 days.

(21) Appl. No.: 18/462,706

(22) Filed: Sep. 7, 2023

(65) Prior Publication Data

US 2024/0075231 A1     Mar. 7, 2024

Related U.S. Application Data

(60) Provisional application No. 63/374,789, filed on Sep. 7, 2022.

(51) Int. Cl.
*A61B 1/267*     (2006.01)
*A61M 16/04*     (2006.01)

(52) U.S. Cl.
CPC ......... *A61B 1/267* (2013.01); *A61M 16/0488* (2013.01)

(58) Field of Classification Search
CPC ....... A61B 1/00135; A61B 1/24; A61B 1/267; A61M 16/0431; A61M 16/0488; A61M 16/049; A61M 16/0495
See application file for complete search history.

(56) References Cited

U.S. PATENT DOCUMENTS

| | | | | |
|---|---|---|---|---|
| 4,919,126 A * | 4/1990 | Baildon | ............ | A61M 16/0497 |
| | | | | 128/207.14 |
| 5,551,946 A * | 9/1996 | Bullard | .................. | A61B 1/267 |
| | | | | 600/187 |
| 8,366,612 B2 * | 2/2013 | Rosenthal | .............. | A61B 1/018 |
| | | | | 600/188 |
| 9,078,615 B2 * | 7/2015 | Young | .................... | A61B 1/267 |
| 9,295,798 B2 * | 3/2016 | Sartore | .................... | A61B 1/05 |
| 2020/0060538 A1 * | 2/2020 | Ferren | .................... | A61B 1/267 |
| 2022/0184334 A1 * | 6/2022 | Chen | ................. | A61M 16/0402 |

OTHER PUBLICATIONS

Frank Furio "Medical Def; What is a Glidescope and How is a Glidescope Used?" https://medicaldef.com/knowledge-base/glidescope-glidescope-intubation/ Mar. 27, 2019; pp. 3.
Harwell Medical "Grandview: Disosable Laryngoscope Blade; See The Cords On Your First Attempt" https://www.hartwellmedical.com/granview-laryngoscope-blades/ retreived from internet Aug. 2, 2022; pp. 4.

* cited by examiner

*Primary Examiner* — Larry E Waggle, Jr.
(74) *Attorney, Agent, or Firm* — Allen, Dyer, Doppelt + Gilchrist, PA

(57) ABSTRACT

A system may include a laryngoscope, and an intubation device configured to guide insertion of the laryngoscope into the throat of a patient. The intubation device may have a proximal end, a distal end, and a medial portion between the proximal and distal ends. The proximal and distal ends may be narrower than the medial portion, and the intubation device may have a first taper from the medial portion to the distal end and a second taper from the medial portion to the proximal end.

15 Claims, 6 Drawing Sheets

ENDOTRACHEAL INTUBATION DEVICE AND RELATED METHODS

RELATED APPLICATIONS

This application claims the benefit of U.S. provisional application Ser. No. 63/374,789 filed Sep. 7, 2022, which is hereby incorporated herein in its entirety by reference.

TECHNICAL FIELD

The present disclosure relates to medical devices, and more particularly, to devices for endotracheal intubation and related methods.

BACKGROUND

Endotracheal Intubation is a medical procedure used to secure the airway of a patient during surgery, or if breathing has become difficult for the patient. For example, this may be the result of an airway blockage, respiratory illness, or trauma.

Laryngoscopes are the traditional instruments used to perform endotracheal intubation. With such devices, when a medical professional needed to open up a patient's airway, the professional would move the patient's tongue aside to view the patient's vocal cords so that the laryngoscope could be properly inserted without damage to the vocal cords. However, because this process can be difficult to perform correctly, there may be an undesirably large number of first-attempt failures. This results not only in additional discomfort and trauma for the patient, but also the potential for injury as well.

As a result, another device from Verathon Inc. called a GlideScope® is now commonly used during endotracheal intubations to help the medical professional better visualize the vocal cords and improve the rate of first-attempt successes. To this end, a GlideScope® includes an endoscopic video camera that helps medical personnel see down a patient's airway. With a GlideScope®, the medical professional inserts a special purpose laryngoscope designed as a guide for the endoscopic camera. The GlideScope® handle is inserted into the patient's mouth, through which the camera may then be inserted to safely guide the Glide-Scope® down the patient's throat.

Despite the existence of such devices, further improvements may be desirable with respect to endotracheal intubation technology to help further assist medical personnel to achieve a higher percentage of first-attempt successes.

SUMMARY

A system may include a laryngoscope, and an intubation device configured to guide insertion of the laryngoscope into the throat of a patient. The intubation device may have a proximal end, a distal end, and a medial portion between the proximal and distal ends. The proximal and distal ends may be narrower than the medial portion, and the intubation device may have a first taper from the medial portion to the distal end and a second taper from the medial portion to the proximal end.

In an example embodiment, the intubation device may define a sleeve configured to at least partially surround the laryngoscope. By way of example, the first and second tapers may be in a range of 15-25% off of the width of the medial portion. Also by way of example, the proximal and distal ends may have a width of 4 cm or less, and the medial portion may have a width of 5 cm or more.

In an example implementation, the laryngoscope may have a curved body, and the intubation device may be curved to correspond with the curved body of the laryngoscope. In some embodiments, the intubation device may have rounded edges on opposing sides thereof. In an example embodiment, the intubation device may be integrally formed with the laryngoscope. By way of example, the laryngoscope may comprise an endoscopic video laryngoscope.

A related apparatus configured to guide insertion of a laryngoscope into the throat of a patient may include a body having a proximal end, a distal end, and a medial portion between the proximal and distal ends. The proximal and distal ends may be narrower than the medial portion, and the body may have a first taper from the distal end to the medial portion and a second taper from the proximal end to the medial portion.

A related method of performing a laryngoscopy may include inserting an intubation device into the throat of a patient having a first taper from a medial portion and a distal end of the intubation device, with the first taper causing swollen tissue within the throat to spread apart as the medial portion progresses into the throat. The method may further include inserting a laryngoscope into the throat using the intubation device to guide the laryngoscope, performing the laryngoscopy with the laryngoscope, and removing the laryngoscope from the throat of the patient. The method may further include removing the intubation device from the throat of the patient, with the intubation device further having a second taper from the medial portion and a proximal end of the intubation device, and the second taper causing swollen tissue within the throat to spread apart as the medial portion is removed from the throat.

DETAILED DESCRIPTION

Example embodiments will now be described more fully hereinafter with reference to the accompanying drawings, in which the example embodiments are shown. The embodiments may, however, be implemented in many different forms and should not be construed as limited to the specific examples set forth herein. Rather, these embodiments are provided so that this disclosure will be thorough and complete. Like numbers refer to like elements throughout, and prime notation is used to indicate similar elements in different embodiments.

Referring initially to FIGS. 1-4, an intubation device or guide 30 for endotracheal intubations is now described. By way of background, despite the improvement that devices such as the GlideScope® provides during typical intubation procedures, in some cases it may still be difficult to achieve first-attempt success and/or to remove the GlideScope® from a patient's airway. For example, in some cases a patient presents with an excessively swollen airway due to an allergic reaction, trauma, etc. In such cases, the swollen tissue may just fold over the blade of a GlideScope®, such that the view of the vocal cords is still obstructed notwithstanding the presence of the camera. In emergency situations, if intubation with a GlideScope® fails then there may be no other option but to perform a cricothyrotomy, which is an emergency procedure to establish an airway by creating an incision in the cricothyroid membrane to access the trachea. However, in addition to the surgical trauma to the patient, a cricothyrotomy is not without further risk, such as excessive bleeding if a patient is on blood thinners, for example. Accordingly, it is desirable to achieve first-attempt success with an endotracheal intubation and avoid cricothyrotomys whenever possible.

Figure 1:
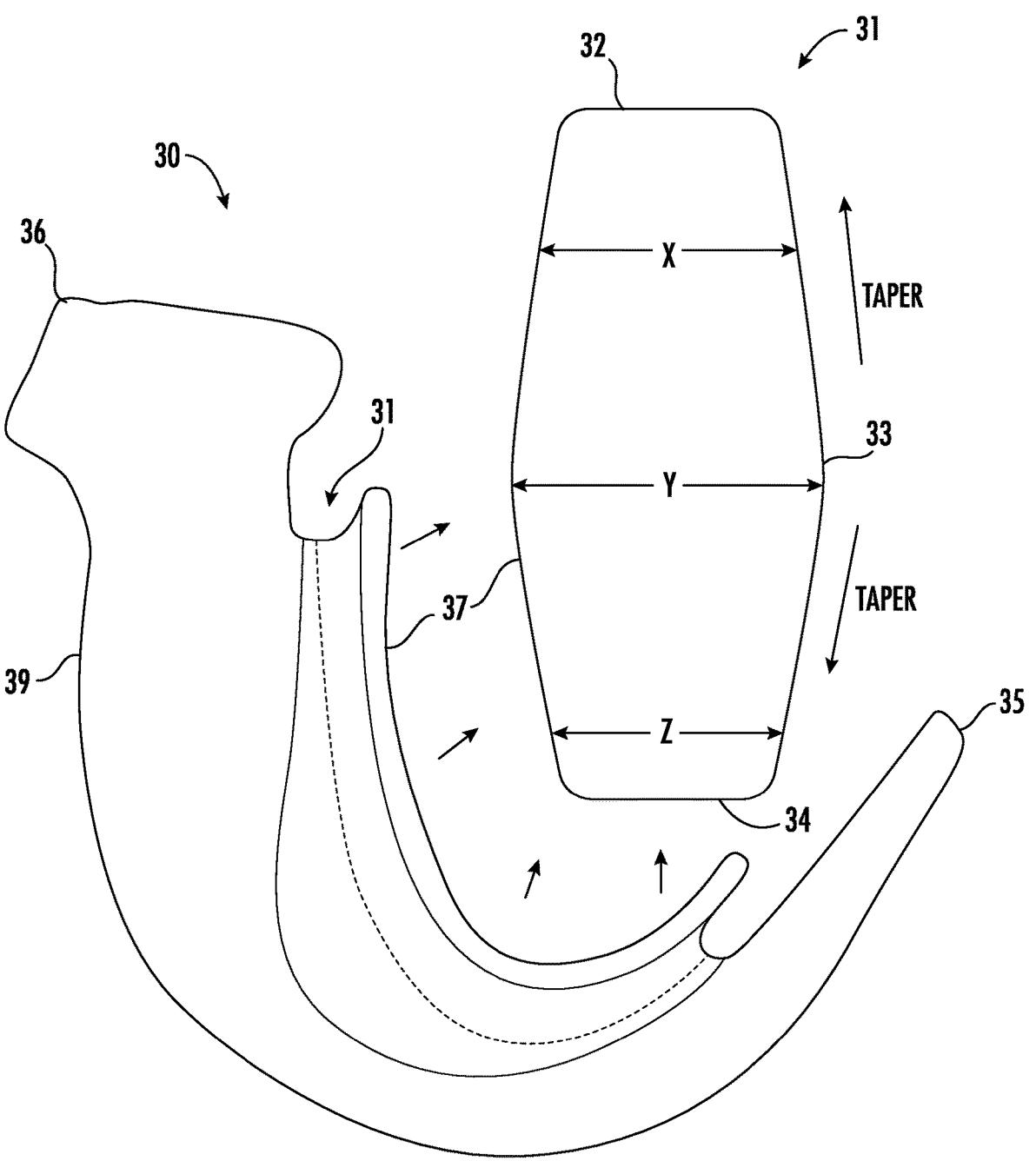
FIG. 1 is a perspective view of an intubation device with an integrated laryngoscope having an endoscopic camera passageway in accordance with an example embodiment.
Figure 2:
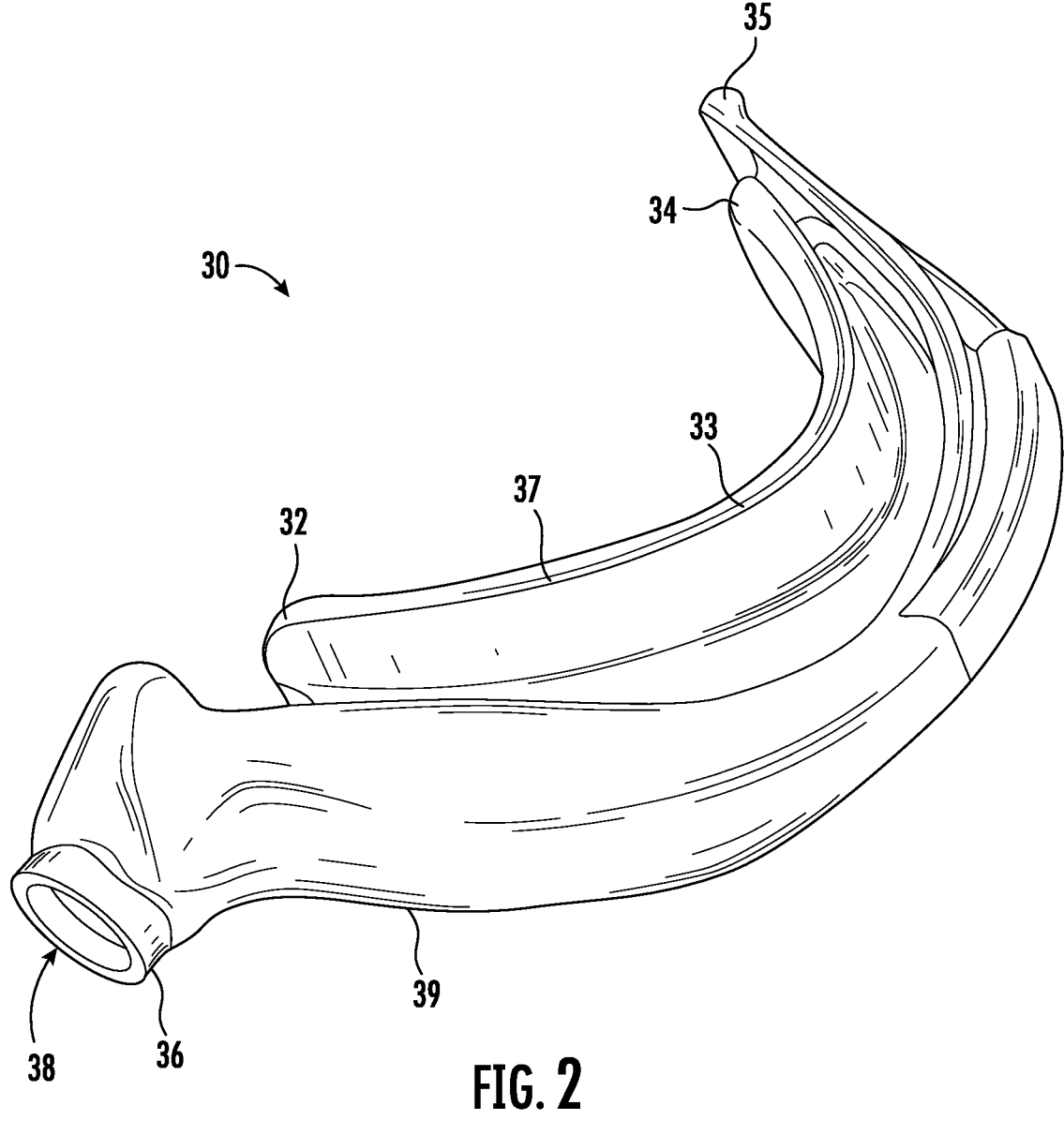
FIGS. 2-4 are perspective views of an example implementation of the intubation device with integrated laryngoscope of FIG. 1.
Figure 3:
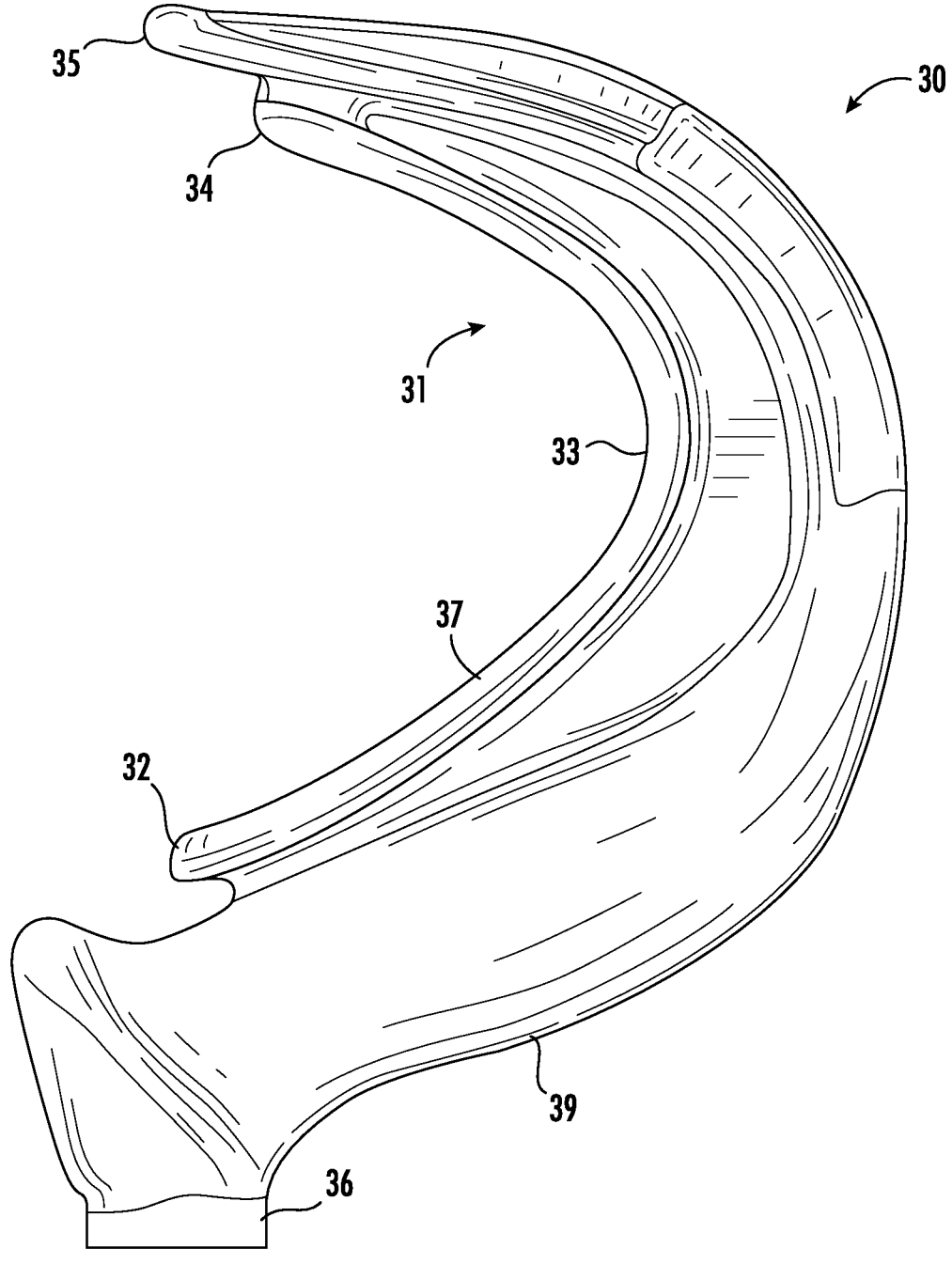
Figure 4:
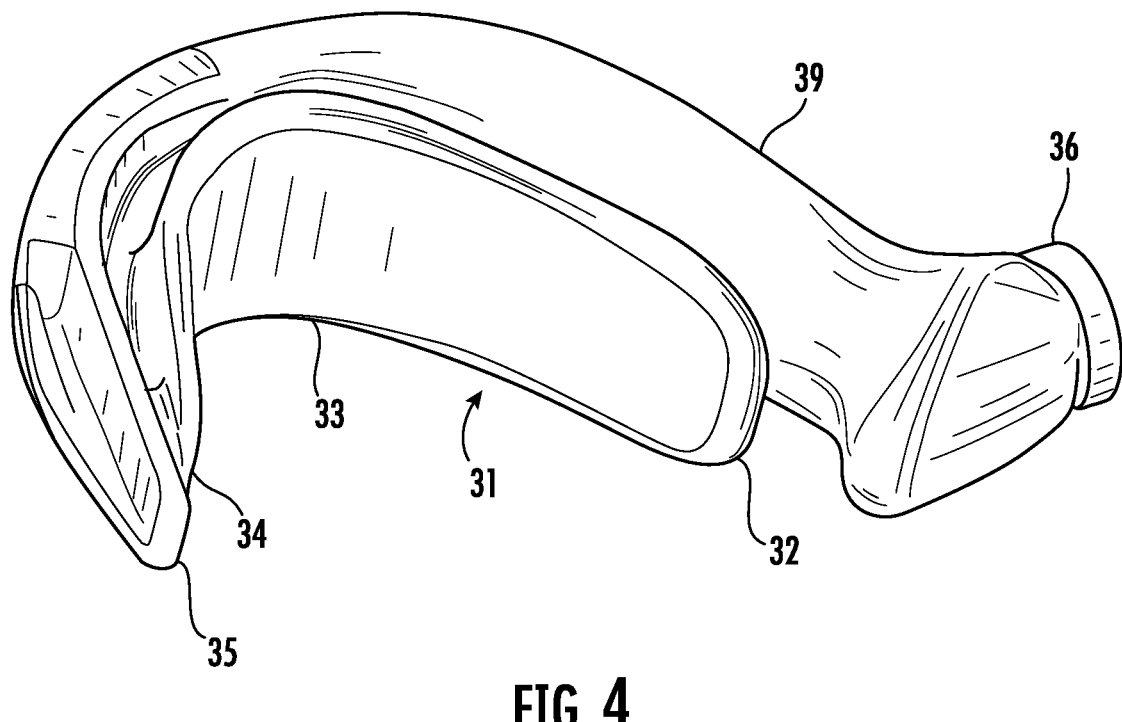

The intubation device 30 illustrated in FIG. 1 includes a blade or sleeve section 31 that tapers from a thicker or wider width y at a medial portion 33 thereof (5.1 cm in the present example) to narrower width x at a proximal end 32 (4.0 cm in the present example). Moreover, the blade section 31 also includes a second taper from the medial portion 33 down to a narrower width z at a distal end 34 (e.g., 4.0 cm). Generally speaking, the tapers may be in a range of about 15-25% in width, and more particularly about 18-22%, although other ranges and widths besides those noted above may be used in different embodiments.

As a tip 35 of the intubation device 30 is inserted into the patient's airway during the intubation procedure, the narrowed distal end 34 enters the swollen tissue of the airway and the blade 31 gradually spreads the tissue apart as the wider medial portion 33 progresses into the tissue to accommodate an integrated passageway 38, which may be swollen as noted above. In the illustrated example, the blade 31 further illustratively includes rounded edges or guide rails 37 on opposing sides thereof to help the swollen tissue more easily slide along the sides/edges. An endoscopic camera (not shown) may then be inserted through a head 36 of the device 30 down the passageway 38 (e.g., a tubular passageway) within a handle 39 of the intubation device 30, which now provides sufficient clearance for the camera to view the vocal cords, and thereby allows the practitioner to insert the tip 35 through the airway without damaging the vocal cords. Once the intubation device 30 is in the final position, the camera may then be removed and a breathing tube may be inserted using the intubation device as a guide.

Yet, once the breathing tube is in place, the problem of the enlarged tissue may still exist. That is, the same difficulty of initially penetrating the enlarged tissue may also otherwise make it difficult to remove a typical laryngoscope or GlideScope® once it is fully inserted. However, because the present intubation device 30 also has a similar taper between the medial portion 33 and the proximal end 32 of the blade section 32, the blade section similarly gradually spreads the enlarged tissue as the blade is carefully pulled out of the patient's airway, in the same manner it was during insertion of the intubation device. The intubation device 30 thereby facilitates removal with reduced risk of trauma to the patient's airway. Considered alternatively, the dual-ended taper of the blade section 31 advantageously provides a tissue expander both for easier pushing edematous tissue out of the way in order to find the epiglottis, as well as for easier removal of the intubation device once the breathing tube is in place. It should be noted that the first and second tapers between the distal end 34, medial portion 33, and proximal end 32 may be of different lengths and have different taper widths in some embodiments, if desired.

Figure 5:
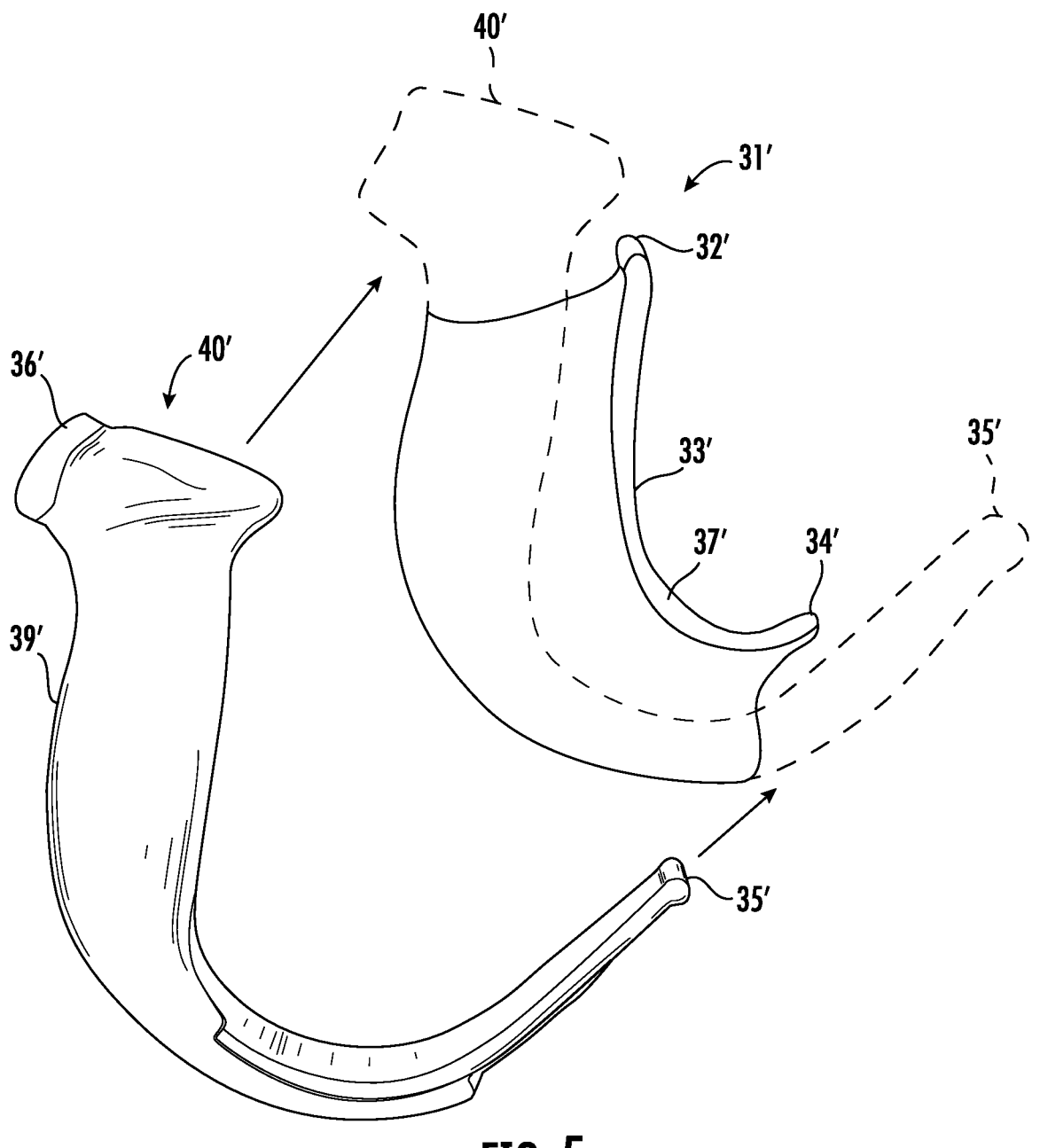
FIG. 5 is a perspective view of an intubation device for use with a separate laryngoscope in accordance with an example embodiment.

Referring additionally to FIG. 5, in another example embodiment the above-described blade section 31' may be formed as a separate piece from the laryngoscope 40' to act as a guide therefor. In other words, the blade section 31' is used in combination with the laryngoscope 40' (a GlideScope® in the present example) in a similar fashion to the integrated intubation device 30 described above with reference to FIGS. 1-4 to serve as a sleeve lift that the laryngoscope slides into. The above-described intubation devices 30, 31' may be formed of a medical grade plastic, for example, such as that used for traditional laryngoscopes.

Figure 6:
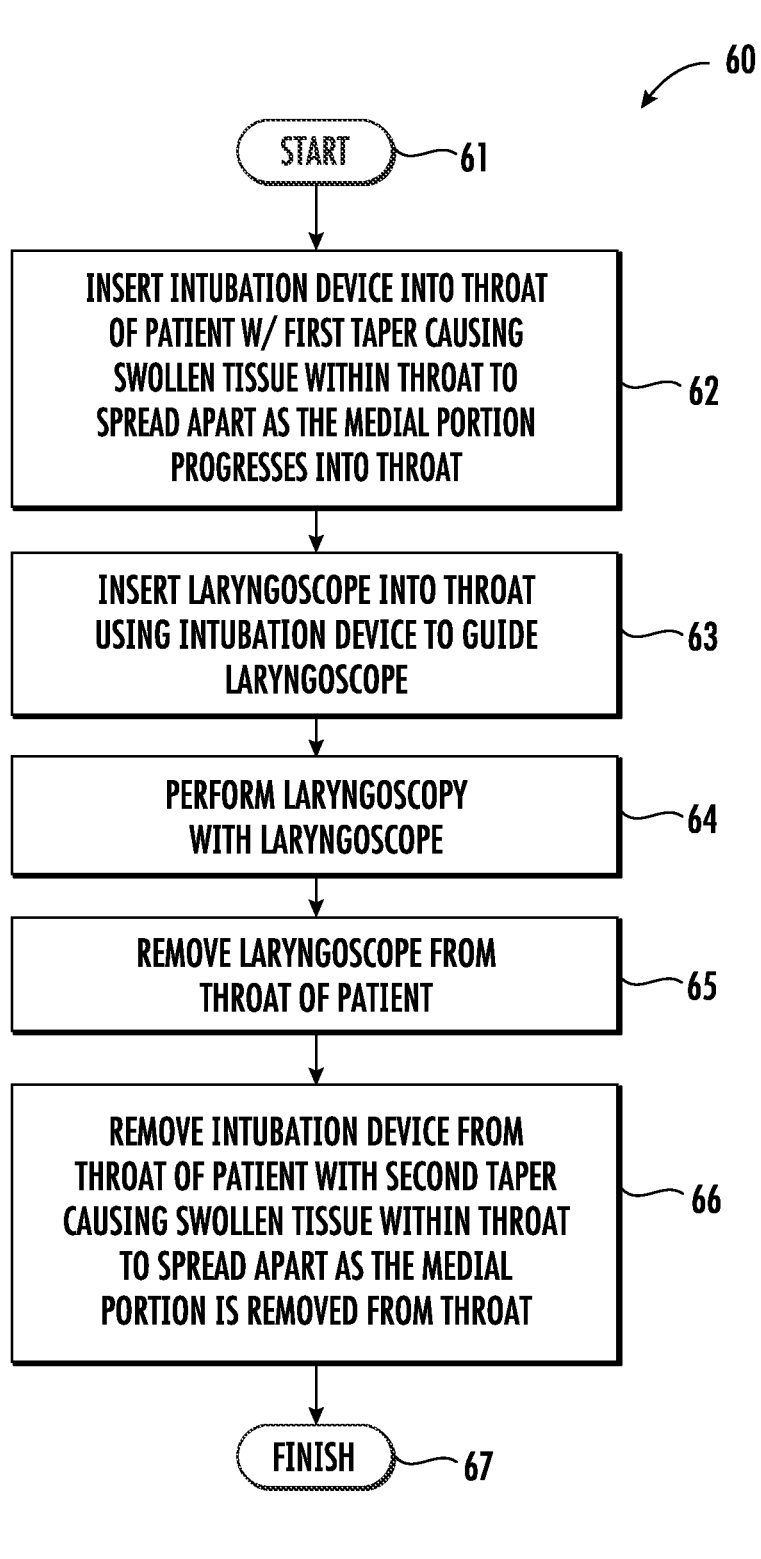
FIG. 6 is a flow diagram illustrating a method of using the intubation device of FIG. 5.

An example approach for using the blade 31' of FIG. 5 is now described with reference to the flow diagram 60 of FIG. 6. Beginning at Block 61, the method begins with inserting the intubation device or blade 31' into the throat of a patient (Block 62), the blade having a first taper between the medial portion 33' and a distal end 34', as discussed above, with the first taper causing swollen tissue within the throat to spread apart as the medial portion progresses into the throat. The method further illustratively includes inserting a laryngoscope 40' into the throat using the intubation device 31' to guide the laryngoscope (Block 63), performing the laryngoscopy with the laryngoscope (Block 64), and removing the laryngoscope from the throat of the patient (Block 65). The method further illustratively includes removing the intubation device 31' from the throat of the patient (Block 66), with the intubation device further having the second taper between the medial portion 33' and a proximal end 32' of the intubation device, and the second taper causing swollen tissue within the throat to spread apart as the medial portion is removed from the throat, as discussed further above. The method of FIG. 6 illustratively concludes at Block 67.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

The invention claimed is:

1. A system comprising:
a laryngoscope; and
an intubation device configured to guide insertion of the laryngoscope into a throat of a patient, the intubation device having a proximal end, a distal end, and a medial portion between the proximal and distal ends;
wherein the intubation device defines a sleeve configured to at least partially surround the laryngoscope;
wherein the laryngoscope has a curved body, and wherein the intubation device is curved to correspond with the curved body of the laryngoscope;
wherein the proximal and distal ends are narrower than the medial portion, and wherein the intubation device has a first taper from the medial portion to the distal end and a second taper from the medial portion to the proximal end; and
wherein the first and second tapers are in a range of 15-25% off of a width of the medial portion, and wherein the proximal and distal ends have a width of 4 cm or less, and the medial portion has a width of 5 cm or more.

2. The system of claim 1 wherein the intubation device comprises rounded edges on opposing sides thereof.

3. The system of claim 1 wherein the intubation device is integrally formed with the laryngoscope.

4. The system of claim 1 wherein the laryngoscope comprises an endoscopic video laryngoscope.

5. The system of claim 1 wherein the first taper and the second taper each comprises a substantially linear taper.

6. The system of claim 5 wherein the substantially linear taper of the first and second tapers extends continuously from the medial portion to the distal end, and from the medial portion to the proximal end, respectively.

7. An apparatus configured to guide insertion of a laryngoscope into a throat of a patient and comprising:

a body having a proximal end, a distal end, and a medial portion between the proximal and distal ends;

wherein the body defines a sleeve configured to at least partially surround the laryngoscope;

wherein the laryngoscope has a curved body, and wherein the body is curved to correspond with the curved body of the laryngoscope;

wherein the proximal and distal ends are narrower than the medial portion, and wherein the body has a first taper from the distal end to the medial portion and a second taper from the proximal end to the medial portion; and wherein the first and second tapers are in a range of 15-25% off of a width of the medial portion, and wherein the proximal and distal ends have a width of 4 cm or less, and the medial portion has a width of 5 cm or more.

8. The apparatus of claim 7 wherein the body comprises rounded edges on opposing sides thereof.

9. The apparatus of claim 7 wherein the first taper and the second taper each comprise a substantially linear taper.

10. The apparatus of claim 9 wherein the substantially linear taper of the first and second tapers extends continuously from the medial portion to the distal end, and from the medial portion to the proximal end, respectively.

11. A method of performing a laryngoscopy comprising:

inserting an intubation device into a throat of a patient having a first taper from a medial portion and a distal end of the intubation device, the first taper causing swollen tissue within the throat to spread apart as the medial portion progresses into the throat;

inserting a laryngoscope into the throat using the intubation device to guide the laryngoscope;

performing the laryngoscopy with the laryngoscope;

removing the laryngoscope from the throat of the patient; and removing the intubation device from the throat of the patient, the intubation device further having a second taper from the medial portion and a proximal end of the intubation device, and the second taper causing swollen tissue within the throat to gradually spread apart as the medial portion is removed from the throat to thereby facilitate removal and reduce trauma risk to the throat;

wherein the intubation device defines a sleeve configured to at least partially surround the laryngoscope when the laryngoscope is inserted into the throat;

wherein the first and second tapers are in a range of 15-25% off of a width of the medial portion; and wherein the proximal and distal ends have a width of 4 cm or less, and the medial portion has a width of 5 cm or more.

12. The method of claim 11 wherein the laryngoscope has a curved body, and wherein the intubation device is curved to correspond with the curved body of the laryngoscope.

13. The method of claim 11 wherein the intubation device comprises rounded edges on opposing sides thereof.

14. The method of claim 11 wherein the first taper and the second taper each comprise a substantially linear taper.

15. The method of claim 14 wherein the substantially linear taper of the first and second tapers extends continuously from the medial portion to the distal end, and from the medial portion to the proximal end, respectively.

* * * * *